United States Patent
Barral et al.

(10) Patent No.: US 9,528,365 B2
(45) Date of Patent: Dec. 27, 2016

(54) APPARATUSES AND METHODS FOR TESTING WELLBORE FLUIDS

(71) Applicant: Schlumberger Technology Corporation, Sugar land, TX (US)

(72) Inventors: Quentin Barral, Clamart (FR); Alice Chougnet-Sirapian, L'Hay les Roses (FR); Bernard Dargaud, Elancourt (FR); Nora Bennani, Paris (FR); Dominique Zamora, Clamart (FR); Slaheddine Kefi, Velizy-Villacoublay (FR)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 251 days.

(21) Appl. No.: 14/283,234

(22) Filed: May 21, 2014

(65) Prior Publication Data

US 2014/0352948 A1    Dec. 4, 2014

(30) Foreign Application Priority Data

Jun. 3, 2013    (EP) .................................... 13305730

(51) Int. Cl.
| | |
|---|---|
| *E21B 47/00* | (2012.01) |
| *E21B 33/13* | (2006.01) |
| *E21B 21/00* | (2006.01) |

(52) U.S. Cl.
CPC ............... *E21B 47/00* (2013.01); *E21B 21/00* (2013.01); *E21B 33/13* (2013.01)

(58) Field of Classification Search
None
See application file for complete search history.

(56) References Cited

U.S. PATENT DOCUMENTS

| | | | |
|---|---|---|---|
| 2008/0163703 A1 | 7/2008 | Boncan et al. | |
| 2010/0242586 A1* | 9/2010 | Elshahawi | ............ E21B 49/082 73/152.39 |
| 2011/0005310 A1 | 1/2011 | Lunkad et al. | |
| 2011/0278004 A1* | 11/2011 | Ali | ......................... C09K 8/524 166/285 |

(Continued)

FOREIGN PATENT DOCUMENTS

WO           00/73620          12/2000

OTHER PUBLICATIONS

Daccord G, Guillot D and Nilsson F: "Mud Removal," in Nelson EB and Guillot D (eds.): Well Cementing—2nd Edition, Houston: Schlumberger (2006) 183-187.

(Continued)

*Primary Examiner* — Andre Allen
(74) *Attorney, Agent, or Firm* — Jeremy D. Tillman; Michael Flynn; Tim Curington

(57) ABSTRACT

An apparatus may be used to test the ability of a first fluid to remove a second fluid from a surface. The apparatus comprises a reservoir that contains the first fluid and a testing cell that contains the second fluid. The testing cell also contains a rotor within. The first fluid is pumped into the testing cell, thereby displacing the second fluid. The displaced second fluid flows to a collection vessel. The apparatus is particularly useful for determining the ability of a chemical wash or a spacer fluid to remove non-aqueous drilling fluids from a metallic surface.

20 Claims, 7 Drawing Sheets

(56) References Cited

U.S. PATENT DOCUMENTS

| | | | |
|---|---|---|---|
| 2012/0048008 A1 | 3/2012 | Pindippolu et al. | |
| 2012/0241155 A1* | 9/2012 | Ali | C09K 8/524 |
| | | | 166/285 |
| 2013/0106106 A1* | 5/2013 | Andujar | F03B 13/00 |
| | | | 290/43 |
| 2014/0216149 A1* | 8/2014 | Zhou | G01N 33/2823 |
| | | | 73/152.18 |
| 2015/0240142 A1* | 8/2015 | Kefi | C09K 8/42 |
| | | | 507/135 |
| 2016/0060500 A1* | 3/2016 | Kefi | C09K 8/06 |
| | | | 507/136 |

OTHER PUBLICATIONS

"Recommended Practice 13B-2 for Field Testing of Oil-Based Drilling Fluids," Washington DC: American Petroleum Institute (2012).

Expanded search report for the equivalent European patent application No. 14001799.7 issued on Nov. 13, 2014.

* cited by examiner

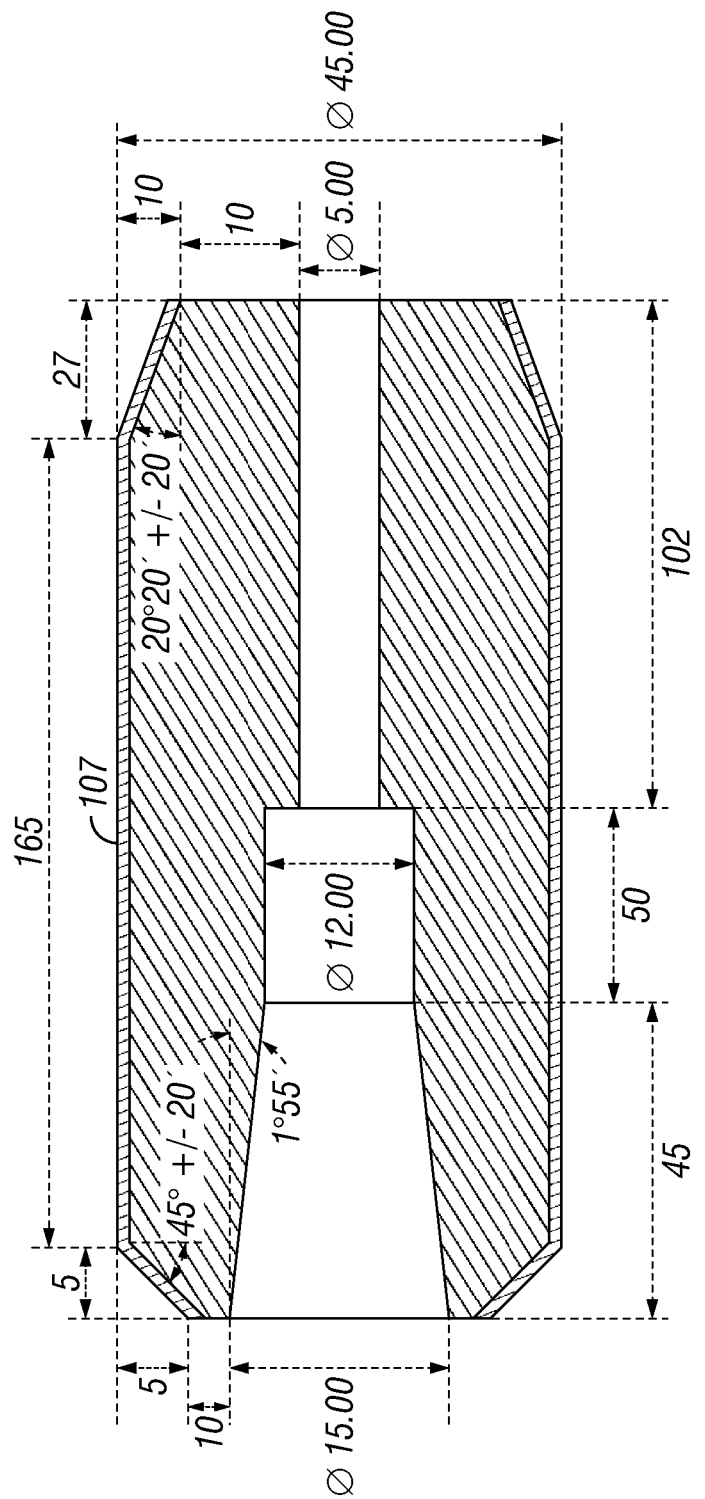

APPARATUSES AND METHODS FOR TESTING WELLBORE FLUIDS

BACKGROUND

The statements in this section merely provide background information related to the present disclosure and may not constitute prior art.

This disclosure relates to apparatuses and methods for testing fluids, in particular, fluid compositions and methods for well-completion operations during which the fluid compositions are pumped into a wellbore and make contact with tubular bodies and subterranean rock formations.

In the course of completing oil and gas wells and the like, various types of fluids are circulated in the wellbore. These fluids include, but are not limited to, drilling fluids, spacer fluids, cement slurries and gravel-packing fluids. In addition, these fluids typically contain solid particles.

Cement slurries are usually incompatible with most drilling fluids. If the cement slurry and drilling fluid commingle, a highly viscous mass may form that can cause several problems. Cement slurry can channel through the viscous mass. Unacceptably high friction pressures can develop during the cement job. Plugging of the annulus can result in job failure. In all of these situations, zonal isolation may be compromised, and expensive remedial cementing may be required.

Consequently, intermediate fluids called preflushes are often pumped as buffers to prevent contact between cement slurries and drilling fluids. Preflushes can be chemical washes that contain no solids or spacer fluids that contain solids and can be mixed at various densities.

Spacers are preflushes with carefully designed densities and rheological properties. Spacers are more complicated chemically than washes. Viscosifiers are necessary to suspend the solids and control the rheological properties, and usually comprise water-soluble polymers, clays or both. Other chemical components include dispersants, fluid-loss control agents, weighting agents, antifoam agents and surfactants. A thorough discussion concerning the uses and compositions of preflushes may be found in the following publication. Daccord G, Guillot D and Nilsson F: "*Mud Removal*," in Nelson E B and Guillot D (eds.): *Well Cementing*—$2^{nd}$ Edition, Houston: Schlumberger (2006) 183-187.

For optimal fluid displacement, the density of a spacer fluid should usually be higher than that of the drilling fluid and lower than that of the cement slurry. Furthermore, the viscosity of the spacer fluid is usually designed to be higher than the drilling fluid and lower than the cement slurry. The spacer fluid must remain stable throughout the cementing process (i.e., no free-fluid development and no sedimentation of solids). In addition, it may be necessary to control the fluid-loss rate.

Another important function of preflushes is to leave the casing and formation surfaces water wet, thereby promoting optimal bonding with the cement. Achieving water-wet surfaces may be challenging, especially when the drilling fluid has been non-aqueous. Such non-aqueous fluids (NAF) may be oil-base muds, synthetic muds or emulsion muds whose external phase is oil-base. For these circumstances, special dispersant and surfactant systems have been developed by the industry. Designing a dispersant/surfactant system for a particular well may be complicated because several parameters must be considered, including the base oil of the NAF, the presence of emulsifiers, the fluid density, bottomhole temperature, presence of brine salts and the chemical nature of the cement system.

Laboratory tests may be performed to determine the ability of dispersants and surfactants to properly remove NAF from the annulus and leave casing surfaces water wet. The most common methods are "grid tests" and "rotor tests." Grids are made from screens with different mesh sizes. Rotors are usually steel cylinders whose surfaces may be smooth, rusty, sandblasted to various degrees of roughness, or covered with a screen. The grid or rotor is first immersed in a NAF, the operator verifies that the surfaces are completely coated, and the grid or rotor is weighed. Then the grid or rotor is immersed in an aqueous solution containing dispersants and surfactants at desired concentrations. The grid or rotor may remain stationary or be agitated in the solution for various time periods. Following the immersion period, the grid or rotor is removed and reweighed. The difference between the original and final weight reveals the percentage of NAF removal and the efficiency of the surfactant/dispersant mixture. This method may not be representative of the process that occurs in a well. The test temperature is limited to about 85° C. (185° F.) because it is performed at ambient pressure. In addition, the test does not allow for the use of spacer fluids or other types of fluids that contain suspended solids. When a grid or rotor coated with a solids-laden NAF is immersed in a solids-laden spacer fluid, the grid or rotor may not be solids free upon removal and measuring a weight difference may not provide useful information concerning how well the spacer displaced the NAF.

SUMMARY

In an aspect, embodiments relate to apparatuses comprising a reservoir containing a piston and a piston rod, at least one thermocouple, heating jackets, a testing cell, a rotor connected to a stirring apparatus with adjustable rotational speed, a collection vessel, a pressurization system, a fluid transport system, one or more valves and a pressure gauge.

In a further aspect, embodiments relate to methods comprising assembling an apparatus that comprises a reservoir containing a piston and a piston rod, at least one thermocouple, heating jackets, a testing cell, a rotor connected to a stirring apparatus, a collection vessel, a pressurization system, a fluid transport system, one or more valves and a pressure gauge. The reservoir is filled with a spacer fluid or chemical wash. The portion of the fluid transport system between the reservoir and the testing cell is filled with spacer fluid or chemical wash. The testing cell is filled with a drilling fluid. The pressurization system is used to pressurize the apparatus. Heating jackets are used to heat the spacer fluid or chemical wash, and the drilling fluid to a desired test temperature. The stirring apparatus is activated such that the rotor spins in the drilling fluid. The piston is activated such that the spacer fluid or chemical wash enters the testing cell and displaces the drilling fluid. Displaced drilling fluid then flows through the portion of the fluid transport system that connects the testing cell to the collection vessel. Drilling fluid displacement continues until the spacer or chemical wash has exited the reservoir. The apparatus is then cooled and depressurized to ambient temperature and pressure. The rotor is removed from the testing cell and immersed in a mutual solvent, thereby cleaning the exterior surface. The mutual solvent is then analyzed to determine the amount of drilling fluid that still coated the exterior surface of the rotor.

BRIEF DESCRIPTION OF THE DRAWINGS

FIG. 5 is a schematic diagram of an embodiment of the rotor of the apparatus.

DETAILED DESCRIPTION

At the outset, it should be noted that in the development of any such actual embodiment, numerous implementation-specific decisions must be made to achieve the developer's specific goals, such as compliance with system related and business related constraints, which will vary from one implementation to another. Moreover, it will be appreciated that such a development effort might be complex and time consuming but would nevertheless be a routine undertaking for those of ordinary skill in the art having the benefit of this disclosure. In addition, the composition used/disclosed herein can also comprise some components other than those cited. In the summary and this detailed description, each numerical value should be read once as modified by the term "about" (unless already expressly so modified), and then read again as not so modified unless otherwise indicated in context. Also, in the summary and this detailed description, it should be understood that a concentration range listed or described as being useful, suitable, or the like, is intended that any and every concentration within the range, including the end points, is to be considered as having been stated. For example, "a range of from 1 to 10" is to be read as indicating each and every possible number along the continuum between about 1 and about 10. Thus, even if specific data points within the range, or even no data points within the range, are explicitly identified or refer to only a few specific, it is to be understood that inventors appreciate and understand that any and all data points within the range are to be considered to have been specified, and that inventors possessed knowledge of the entire range and all points within the range.

The Applicant has discovered improved apparatuses and methods for performing tests that determine the ability of a fluid to remove another fluid, particularly NAF, from surfaces.

In an aspect, embodiments relate to apparatuses for determining the ability of first fluid to remove a second fluid from a surface. Schematic diagrams of one embodiment are presented in FIGS. 1-5.

Figure 1:
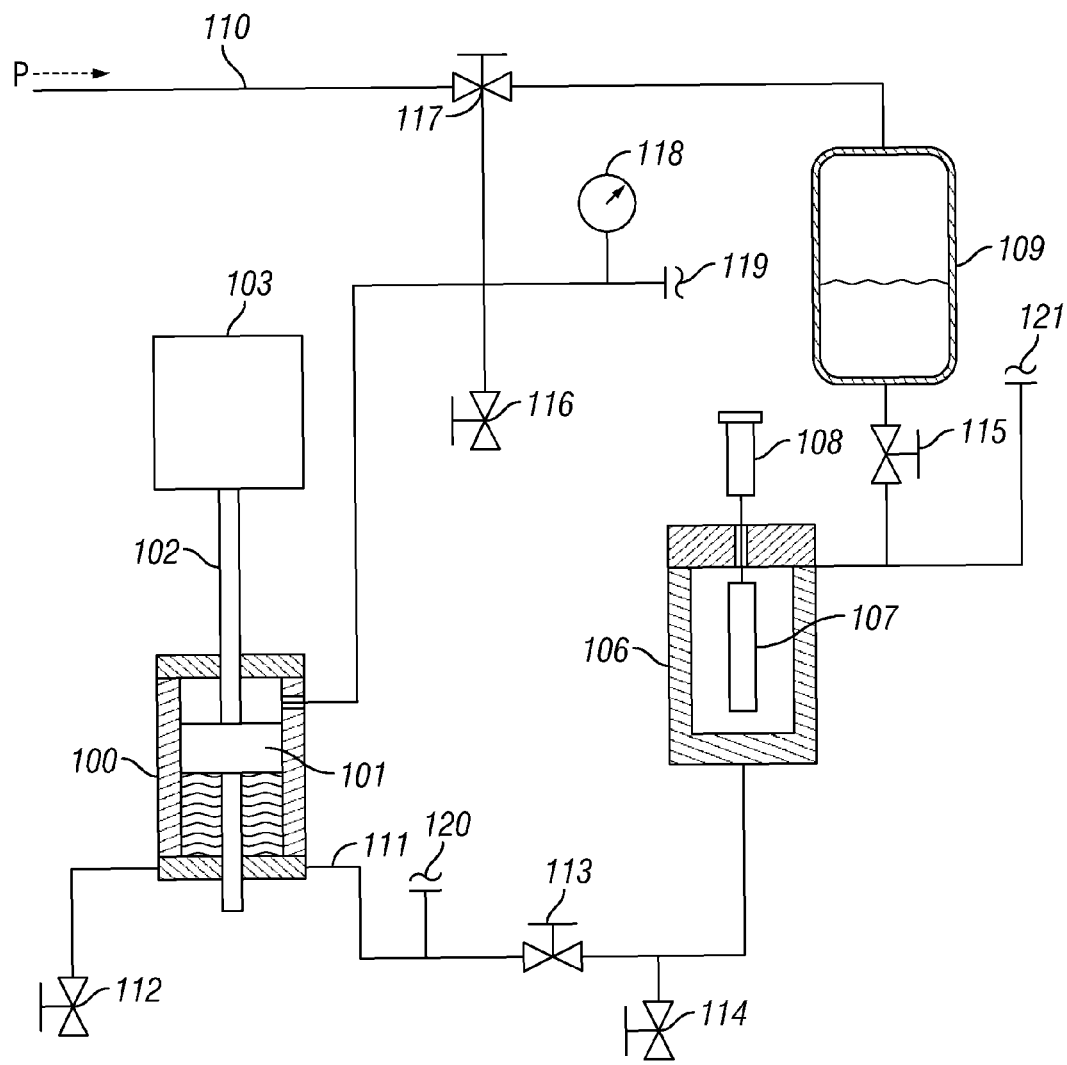
FIG. 1 is a schematic diagram of an embodiment of the disclosed apparatus.

FIG. 1 is a general view of the system. A reservoir 100 contains a piston 101 and a piston rod 102. The reservoir contains a first fluid (e.g., a chemical wash or spacer fluid) to be evaluated. The apparatus may further comprise a piston displacement control system 103 that can be operated pneumatically, hydraulically or electrically. A testing cell 106 initially holds a second fluid (e.g., a drilling fluid, NAF in particular). Inside the testing cell 106 is a rotor 107 that is connected to a stirring apparatus with adjustable rotational speed 108. In this document, a "rotor" may be a cylindrical device, a coupon, a rock or a device with a rock coating. The rotor may be fabricated from carbon steel, stainless steel or other materials of the art used to fabricate equipment that is placed in a wellbore. The rotor surface may be smooth, rusty, sandblasted or covered with a grid. A collection vessel 109 is initially empty, and receives displaced second fluid that exits the testing cell 106.

The apparatus is pressurized by a pressurization system 110. In this particular embodiment, nitrogen gas or an inert gas is used to apply pressure to the apparatus. The pressurization system is directly connected to the reservoir 100, a pressure gauge 118 and the collection vessel 109. Valves 116 and 117 control the flow of gas, and the system is protected by a rupture disk 119. The first and second fluids flow through a fluid transport system 111. Flow through the fluid transport system is controlled by valves 112, 113, 114 and 115, and the system is protected by rupture disks 120 and 121. Fluids envisioned for testing in the apparatus include drilling fluids, spacer fluids, chemical washes, cement slurries, gravel packing fluids and stimulation fluids.

Other devices that may be incorporated in the apparatus include sensors for detecting and characterizing the displacement of fluids, such as conductivity and density sensors.

Figure 2:
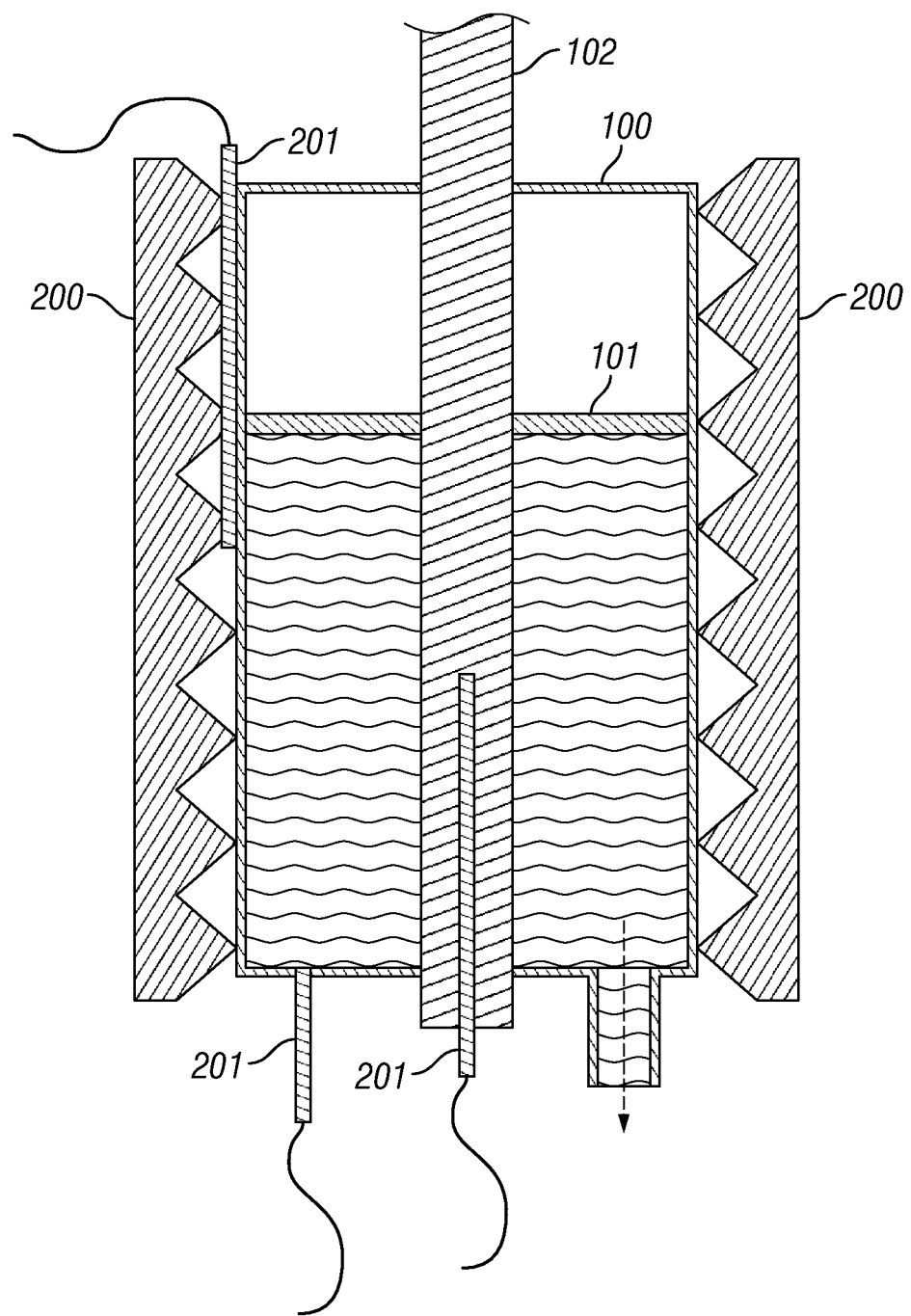
FIG. 2 is a detailed diagram of an embodiment of the reservoir of the apparatus.

FIG. 2 is a more detailed view of the reservoir 100. The reservoir is surrounded by a heating jacket 200 and at least one thermocouple 201 is installed for monitoring the reservoir temperature.

Figure 3:
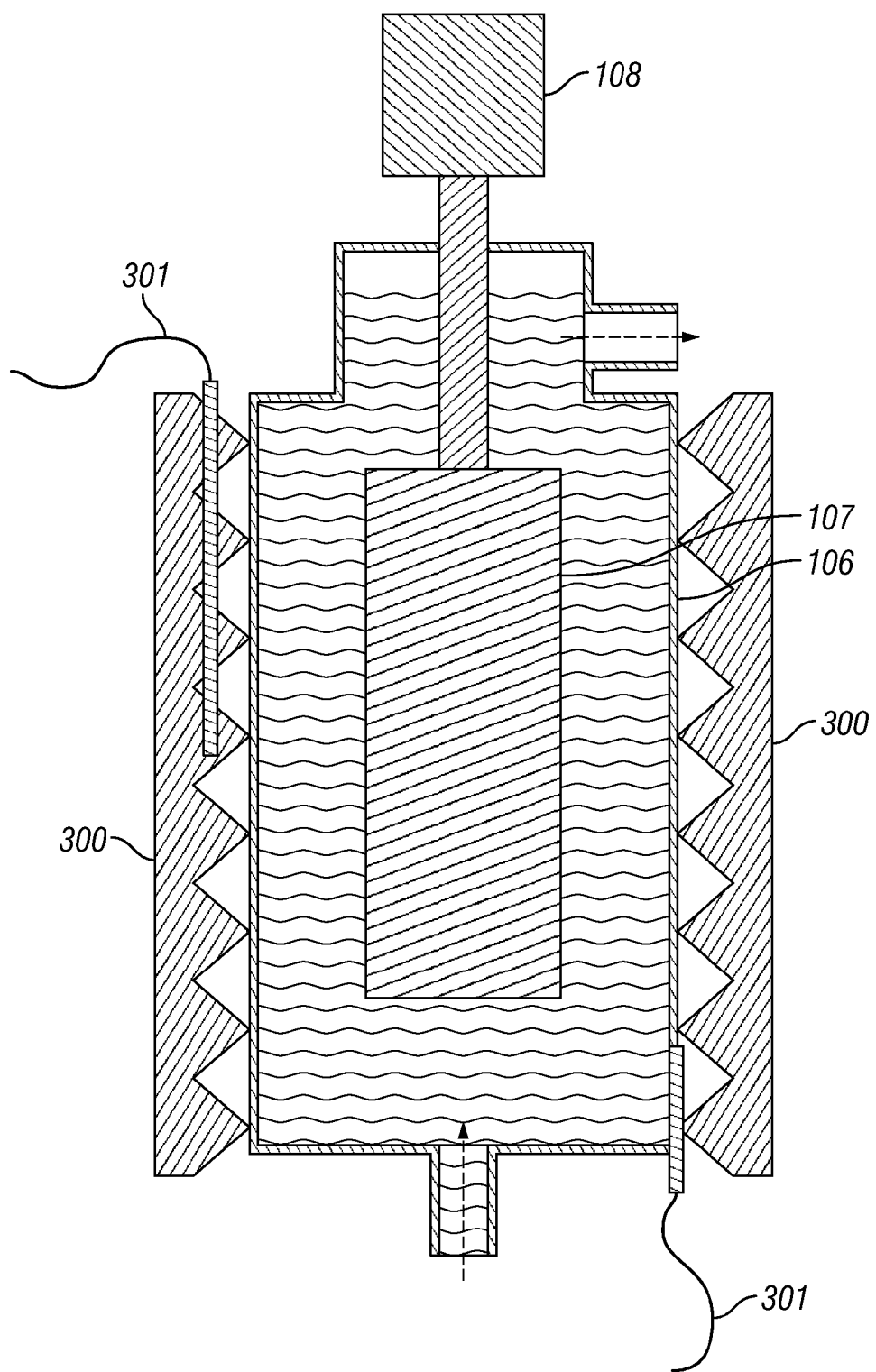
FIG. 3 is a detailed diagram of an embodiment of the testing cell of the apparatus.

FIG. 3 is a more detailed view of the testing cell 106. The cell is surrounded by a heating jacket 300 and at least one thermocouple 301 is installed for monitoring the cell temperature. There may also be a tapered seat (not shown) installed at the bottom of the cell interior that may keep the rotor centered as it rotates.

Figure 4A:
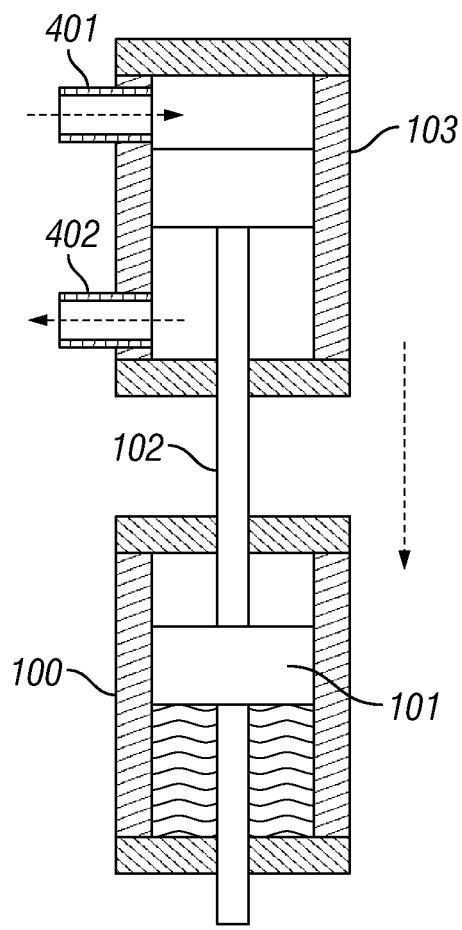
FIGS. 4A and 4B illustrate the operation of a pneumatically controlled piston displacement control system.
Figure 4B:
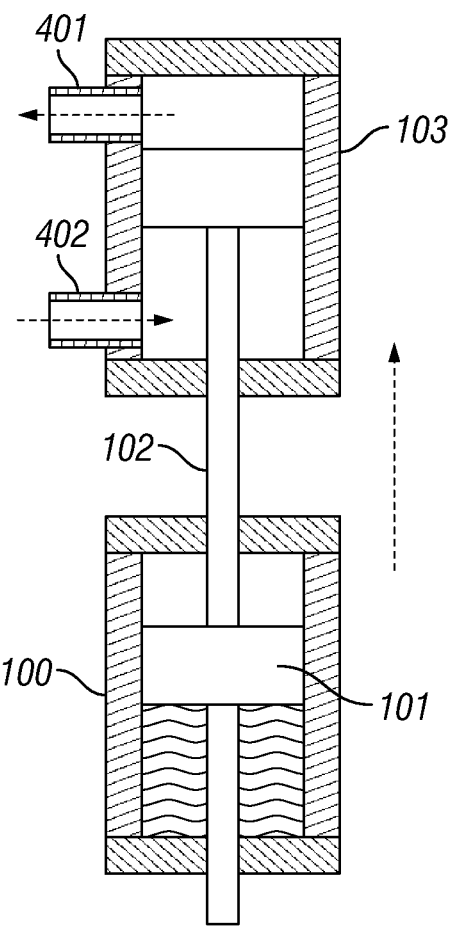

FIGS. 4A and 4B show an embodiment of a piston displacement control system 103 that operates pneumatically. The system comprises an internal chamber having a top port 401 and a bottom port 402. As shown in FIG. 4A, air may flow into port 104, thereby forcing the piston downward and displacing air that exits the chamber through port 105. Conversely, as shown in FIG. 4B, the piston may be forced upward by reversing the direction of air flow in the chamber.

FIG. 5 is a more detailed view of an embodiment of the rotor 107. The linear dimensions are in mm. Those skilled in the art will recognize that rotors with alternate linear and angular rotor dimensions may be substituted for the one pictured here, depending upon the well conditions and profiles envisioned by testing personnel. The rotor may be fabricated from carbon steel or stainless steel; however, other materials used in well operations may be substituted as is known in the art. The rotor surface may be smooth or treated such that the surface is irregular. Such treatment may include rusting, sandblasting to various degrees of roughness, and the installation of grid-like materials with various mesh sizes. Other methods for forming an irregular surface may be employed as is known in the art.

In a further aspect, embodiments relate to methods for determining the ability of a first fluid to remove a second fluid from a surface. An apparatus, described in an earlier aspect of this document, is assembled. The reservoir 100 is filled with the first fluid. The portion of the fluid transport system 111 that connects the reservoir 100 to the testing cell 106 is also filled with the first fluid. The testing cell 106 is filled with the second fluid. The rotor 107 is placed in the testing cell 106 and connected to the stirring apparatus 108. The testing cell 106 is then closed.

The pressurization system is used to pressurize the apparatus to a desired pressure. Heating jackets 200 and 300 are used to heat the first and second fluids to desired temperatures. The stirring apparatus 108 is activated such that the rotor 107 spins in the second fluid. The piston 101 is activated such that the first fluid enters the testing cell 106 and displaces the second fluid. The displaced second fluid is allowed to flow through the portion of the fluid transport system 111 that connects the testing cell 106 to the collection vessel 109. Displacement of the second fluid continues until the first fluid has exited the reservoir 100. The apparatus is cooled and depressurized to ambient temperature and pressure. The rotor 107 is removed from the testing cell 106. The rotor 107 is then immersed in a solvent, thereby cleaning the exterior surface of the rotor 107. The solvent containing residue from the exterior surface of the rotor is then analyzed to determine the amount of second fluid that still remained on the exterior surface of the rotor 107.

The first fluid may be chemical wash or a spacer fluid. The second fluid may be a drilling fluid, a NAF in particular. The NAF second fluid may be a water-in-oil emulsion. However, those skilled in the art will recognize that other types of wellbore fluids such as displacement fluids, cement slurries, gravel-packing fluids and stimulation fluids may be tested in the apparatus.

Nitrogen gas may be used to pressurize the pressurization system 110. However, as is known in the art, other inert gases or liquid fluids may be used for the same purpose.

The surface of the rotor may smooth, rusty sandblasted to a desired degree of roughness or have a grid surface with a desired mesh size. Furthermore, the rotor may be substituted by other testing media known in the art such as a coupon, a rock or a device with a rock surface.

The solvent may be a mutual solvent. The solvent may be a monobutyl ether such as ethylene glycol monobutyl ether (2-butoxyethanol). The determination of residual second fluid in the mutual solvent may be performed by chloride titration, described in detail later in this document.

A description of the operation of one embodiment of the apparatus is given below. This particular embodiment employs a piston displacement control system that operates pneumatically as shown in FIG. 4. In the apparatus constructed by the Applicant, the volumes of the reservoir, test cell and collection cell are 1.2 L, 160 mL and 2.14 L, respectively. Each step is accompanied by a chart indicating the positions of the ports and valves.

Test Preparation

Filling the Reservoir 100 with the First Fluid.

The piston 101 is placed at the bottom of the reservoir 100. The portion of the fluid transport system 111 coming out of the reservoir (between the reservoir and valve 112) is dipped into a beaker containing at least 1.3 L of the first fluid. The piston 101 is pulled up pneumatically and the resulting suction draws the first fluid into the reservoir. The piston velocity is carefully controlled to avoid entry of air into the reservoir 100.

| Port or Valve | 401 | 402 | 112 | 113 | 114 | 115 | 116 | 117 |
|---|---|---|---|---|---|---|---|---|
| Status (Open [O]/Closed [C]) | out | in | O | C | C | O | O | C |

Filling the Fluid Transport System Between the Reservoir 100 and the Testing Cell 106.

Valve 112 is closed, valve 113 is opened and the direction of air flow is reversed in the piston displacement control system 103. This causes the first fluid to flow from the reservoir 100 to the testing cell 106. Flow is stopped when the operator sees the first fluid reach the testing cell. Valve 113 is then closed.

| Port or Valve | 401 | 402 | 112 | 113 | 114 | 115 | 116 | 117 |
|---|---|---|---|---|---|---|---|---|
| Status (Open [O]/Closed [C]) | in | out | C | O | C | O | O | C |

Filling the Testing Cell 106 with the Second Fluid.

Using a syringe, 160 mL of the second fluid is placed in the testing cell 106. Then the testing cell 106 is sealed with a cap to which the rotor 107 is attached, such that the rotor 107 is immersed in the second fluid.

| Port or Valve | 401 | 402 | 112 | 113 | 114 | 115 | 116 | 117 |
|---|---|---|---|---|---|---|---|---|
| Status (Open [O]/Closed [C]) | No flow | No flow | C | C | C | O | O | C |

Preparing to Launch the Experiment.

Valve 113 is reopened, valve 116 is closed and valve 117 is opened in order to apply the desired pressure to the system. In this particular embodiment the maximum working pressure is 20 bar. The rupture disks 120 and 121 are set to to release at 25 bar. For added safety, the apparatus is enclosed inside a protective box. Heating jackets 200 and 300 are activated, and the reservoir and testing cell are heated to the desired temperatures. At this point the testing cell 106 is filled with the second fluid and the reservoir 100 is filled with the first fluid. In addition, the rotor 107 surface is covered with the second fluid.

| Port or Valve | 401 | 402 | 112 | 113 | 114 | 115 | 116 | 117 |
|---|---|---|---|---|---|---|---|---|
| Status (Open [O]/Closed [C]) | No flow | No flow | C | O | C | O | C | O |

Performing the Test

Displacing and Collecting the Fluids.

The stirring apparatus 108 is activated and the rotor 107 rotates at a desired speed (from 20 to 2000 RPM). The pneumatic piston displacement control system 103 is reactivated such that the piston 101 travels downward, forcing the first fluid out of the reservoir 100 and into the testing cell 106. The test is finished when the piston 101 reaches the lowest position in the reservoir 100. Ports 401 and 402 are closed and heating is stopped. When the apparatus cools to ambient temperature, pressure is released by closing valve 117 and slowly opening valve 116. Valves 113 and 115 are closed to avoid flowback of the fluids.

| Port or Valve | 401 | 402 | 112 | 113 | 114 | 115 | 116 | 117 |
|---|---|---|---|---|---|---|---|---|
| Status (Open [O]/Closed [C]) | in | out | C | O | C | O | C | O |

Evaluating the Result

Evaluation of the Rotor 107 Surface after Fluid Displacement.

Valve 114 is opened and the cap and rotor 107 are removed from the testing cell 106. Residual fluid on the rotor 107 is dipped into 100 mL of a mutual solvent in a test tube, ethylene glycol monobutyl ether. The rotor 107 is rotated manually and the test tube is shaken until to rotor surface is clean. The solvent containing the residual fluid from the rotor 107 may then be analyzed such that the amount of second fluid left on the rotor 107 may be determined.

| Port or Valve | 401 | 402 | 112 | 113 | 114 | 115 | 116 | 117 |
|---|---|---|---|---|---|---|---|---|
| Status (Open [O]/Closed [C]) | No flow | No flow | C | C | O | C | O | C |

Many NAF are water-in-oil emulsions and the aqueous phase contains one or more chloride salts. Therefore, if such a NAF is the second fluid in the previously described methods, and the first fluid does not contain chloride salts, measuring the chloride concentration in the mutual solvent will allow operators to determine how effectively the first fluid removed the second one.

Applicants have adapted a chloride titration method published by the American Petroleum Institute (API): *"Recommended Practice 13B-2 for Field Testing of Oil-Based Drilling Fluids,"* 4th Edition, Washington D.C.: American Petroleum Institute (2012).

The method employs the following equipment and reagents: a 500-mL Erlenmeyer flask, a magnetic stirrer, distilled water, a mutual solvent, potassium chromate indicator (5% aqueous solution) and a 0.028N or 0.282N silver nitrate solution.

The mutual solvent solution containing the residual NAF from the rotor 107 is placed in the Erlenmeyer flask. 200 mL of distilled water is then added along with 10 to 15 drops of the potassium chromate indicator. The fluid is stirred rapidly with the magnetic stirrer. While stirring, the fluid is slowly titrated with the silver nitrate solution until the first color change occurs—a salmon-pink color remains stable for at least one minute. This is the end point. Record the volume of silver nitrate solution used.

EXAMPLES

Example 1

Calibration experiments were performed by conducting chloride-ion titrations with known volumes of NAF. The NAF was VERSACLEAN™, available from MI-SWACO, Houston, Tex., USA. The NAF density was 1500 kg/m$^3$ (12.5 lbm/gal). The formulation is described in Table 1.

TABLE 1

Composition of NAF Used for Chloride Titration Experiments

| Components | Concentration g/L [lbm/bbl] | Properties |
|---|---|---|
| EXXSOL D100[1] | 482 [169] | Mineral Oil |
| VERSAMUL[2] | 11.4 [4] | Emulsifier |
| VERSACOAT[2] | 17.1 [6] | Wetting Agent |
| Lime | 28.5 [10] | |
| VG Plus[2] | 8.6 [3] | Organophilic Clay |
| Water | 157 [55] | |
| Calcium Chloride | 41.3 [14.5] | |
| Barite | 756 [265] | Weighting Material |
| Hymod Prima[3] | 50 [17.5] | Fine Silicate Particles |

TABLE 1-continued

Composition of NAF Used for Chloride Titration Experiments

| Components | Concentration g/L [lbm/bbl] | Properties |
|---|---|---|
| Oil/Water Ratio | 80/20 | |
| CaCl$_2$ % | 20 | |

[1]Trademark of ExxonMobil;
[2]Trademark of MI-SWACO;
[3]Trademark of Imerys

Figure 6:
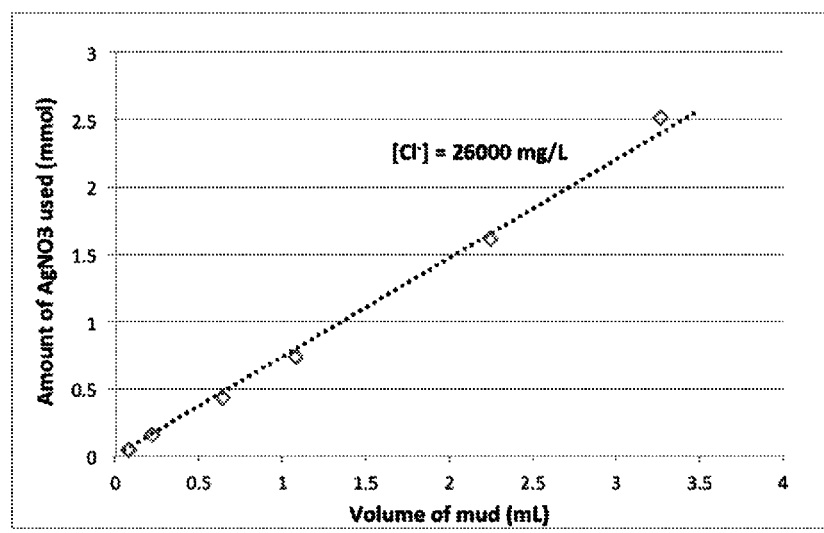
FIG. 6 is a calibration plot for a chloride titration method to determine the concentration of a NAF that contains chloride salts.

The chloride concentration in the VERSACLEAN fluid was 26,000 mg/L. The volume of NAF during the titrations varied from 0 to 3.5 mL. The amount of silver chloride solution required to reach the endpoint is plotted versus the NAF volume in FIG. 6. The results showed all points to be on the same slope (correlation factor R2=0.9998).

Example 2

Figure 7:
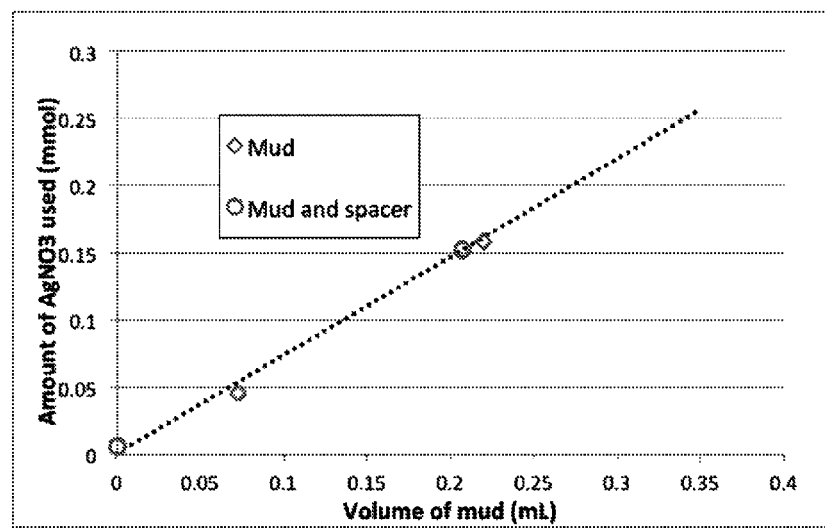
FIG. 7 is a chloride-titration plot for a NAF that has been contaminated by a chloride-free spacer fluid.

Titration experiments were performed with the NAF fluid of Example 1, contaminated with 3 mL of a chloride-free, 1680-kg/m$^3$ spacer fluid. The spacer fluid was MUD-PUSH™ spacer, available from Schlumberger. Barite was used as the weighting material to adjust the fluid density. As shown in FIG. 7, the presence of spacer fluid had no significant effect on the result, and corresponded to points from Example 1 in which only water or 0.21 mL of NAF were present. Therefore, the titration method is valid for evaluating ability of a fluid to remove NAF from a rotor in the testing methods described herein.

Although various embodiments have been described with respect to enabling disclosures, it is to be understood that this document is not limited to the disclosed embodiments. Variations and modifications that would occur to one of skill in the art upon reading the specification are also within the scope of the disclosure, which is defined in the appended claims.

The invention claimed is:

1. An apparatus, comprising:
   (i) a reservoir containing a piston and a piston rod;
   (ii) a testing cell;
   (iii) a rotor connected to a stirring apparatus with an adjustable rotational speed, the rotor and stirring apparatus placed inside of the testing cell;
   (iv) a collection vessel;
   (v) a pressurization system directly connected to the reservoir;
   (vi) a fluid transport system;
   (vii) a pressure gauge; and
   (viii) a piston displacement control system,
   wherein the piston rod is attached to the piston and the piston displacement control system, and the pressure gauge, the reservoir, the testing cell, and the collection vessel are connected to each other by the fluid transport system having at least one valve.

2. The apparatus of claim 1, further comprising at least one heating jacket.

3. The apparatus of claim 1, further comprising at least two thermocouples—one thermocouple attached to the testing cell, and the other thermocouple attached to the reservoir.

4. The apparatus of claim 1, wherein the piston displacement control system is operated pneumatically and has a top port and a bottom port.

5. The apparatus of claim 1, wherein the piston displacement control system is operated hydraulically or electrically.

6. The apparatus of claim 1, wherein nitrogen or an inert gas pressurizes the pressurization system.

7. The apparatus of claim 1, wherein a torque measurement system is connected to the stirring apparatus.

8. The apparatus of claim 1, wherein the rotor has an exterior surface that is smooth, rusty, sandblasted or covered with a grid.

9. The apparatus of any one of claims 1-6, wherein the rotor is fabricated from rock or has a rock surface.

10. A method, comprising:
   (i) assembling an apparatus comprising
      (1) a reservoir containing a piston and a piston rod;
      (2) a testing cell;
      (3) a rotor connected to a stirring apparatus with an adjustable rotational speed, the rotor and stirring apparatus placed inside of the testing cell;
      (4) a collection vessel;
      (5) a pressurization system directly connected to the reservoir;
      (6) a fluid transport system;
      (7) a pressure gauge; and
      (8) a piston displacement control system;
   wherein the piston rod is attached to the piston and the piston displacement control system, and the pressure gauge, the reservoir, the testing cell, and the collection vessel are connected to each other by the fluid transport system having at least one valve;
   (ii) filling the reservoir with a first fluid;
   (iii) filling the testing cell with a second fluid;
   (iv) placing the rotor into the testing cell and connecting the rotor to the stirring apparatus;
   (v) activating the stirring apparatus such that the rotor spins in the second fluid;
   (vi) activating the piston such that the first fluid enters the testing cell and displaces the second fluid;
   (vii) allowing displaced second fluid to flow through a portion of the fluid transport system that connects the testing cell to the collection vessel;
   (viii) continuing to displace the second fluid until the first fluid has exited the reservoir;
   (ix) immersing the rotor in a solvent, thereby cleaning the exterior surface of the rotor;
   (x) analyzing the mutual solvent and determining the amount of second fluid remaining on the exterior surface of the rotor.

11. The method of claim 10, wherein the apparatus further comprises at least two thermocouples—one thermocouple attached to the testing cell, and the other thermocouple attached to the reservoir.

12. The method of claim 10, wherein the apparatus further comprises at least one heating jacket.

13. The method of claim 11, further comprising heating the first and second fluids to desired test temperatures.

14. The method of claim 10, wherein the first fluid is a chemical wash or a spacer fluid.

15. The method of claim 10, wherein the second fluid is a drilling fluid.

16. The method of claim 10, wherein the second fluid is a water-in-oil emulsion.

17. The method of claim 10, wherein nitrogen gas pressurizes the pressurization system.

18. The method of claim 10, wherein the rotor has an exterior surface that is smooth, rusty, sandblasted or covered with a grid.

19. The method of any one of claim 10, wherein the rotor is fabricated from rock or has a rock surface.

20. The method of claim 10, wherein determining the amount of second fluid in the mutual solvent is performed by calcium titration, chloride titration, infrared spectroscopy or a retort test wherein water and oil are collected.

* * * * *